United States Patent [19]
Bloedau

[11] Patent Number: 5,938,629
[45] Date of Patent: Aug. 17, 1999

[54] ADJUSTABLE HINGE STRUCTURE

[75] Inventor: Clarence R. Bloedau, Ft. Worth, Tex.

[73] Assignee: Restorative Care of America Incorporated, Clearwater, Fla.

[21] Appl. No.: 09/057,881

[22] Filed: Apr. 9, 1998

[51] Int. Cl.$^6$ ........................................... A61F 5/00
[52] U.S. Cl. ............................................... 602/16
[58] Field of Search ........................... 602/5, 16, 20, 602/23, 26; 16/284, 325, 327

[56] References Cited

U.S. PATENT DOCUMENTS

| | | | |
|---|---|---|---|
| 2,812,961 | 11/1957 | Brown et al. | 602/16 |
| 3,058,148 | 10/1962 | Beierbach et al. | |
| 5,399,154 | 3/1995 | Kipnis et al. | 602/26 |
| 5,421,810 | 6/1995 | Davis et al. | 602/16 |
| 5,460,599 | 10/1995 | Davis et al. | 602/26 |

*Primary Examiner*—Linda C.M. Dvorak
*Attorney, Agent, or Firm*—Zarley, McKee, Thomte, Voorhees & Sease

[57] ABSTRACT

A hinge structure has first and second hinge elements having inner and outer ends with the inner ends being pivotally secured together. One of said hinge elements has a series of ratchet teeth associated therewith. The other hinge element has a keeper element slidably mounted thereon to engage, and to be disengaged, with the ratchet teeth to cause the hinge elements to be locked and unlocked, respectively, to each other. A cam element on the hinge structure is operatively connected to the keeper element to slidably move the keeper element into or out of engagement with the ratchet teeth.

4 Claims, 5 Drawing Sheets

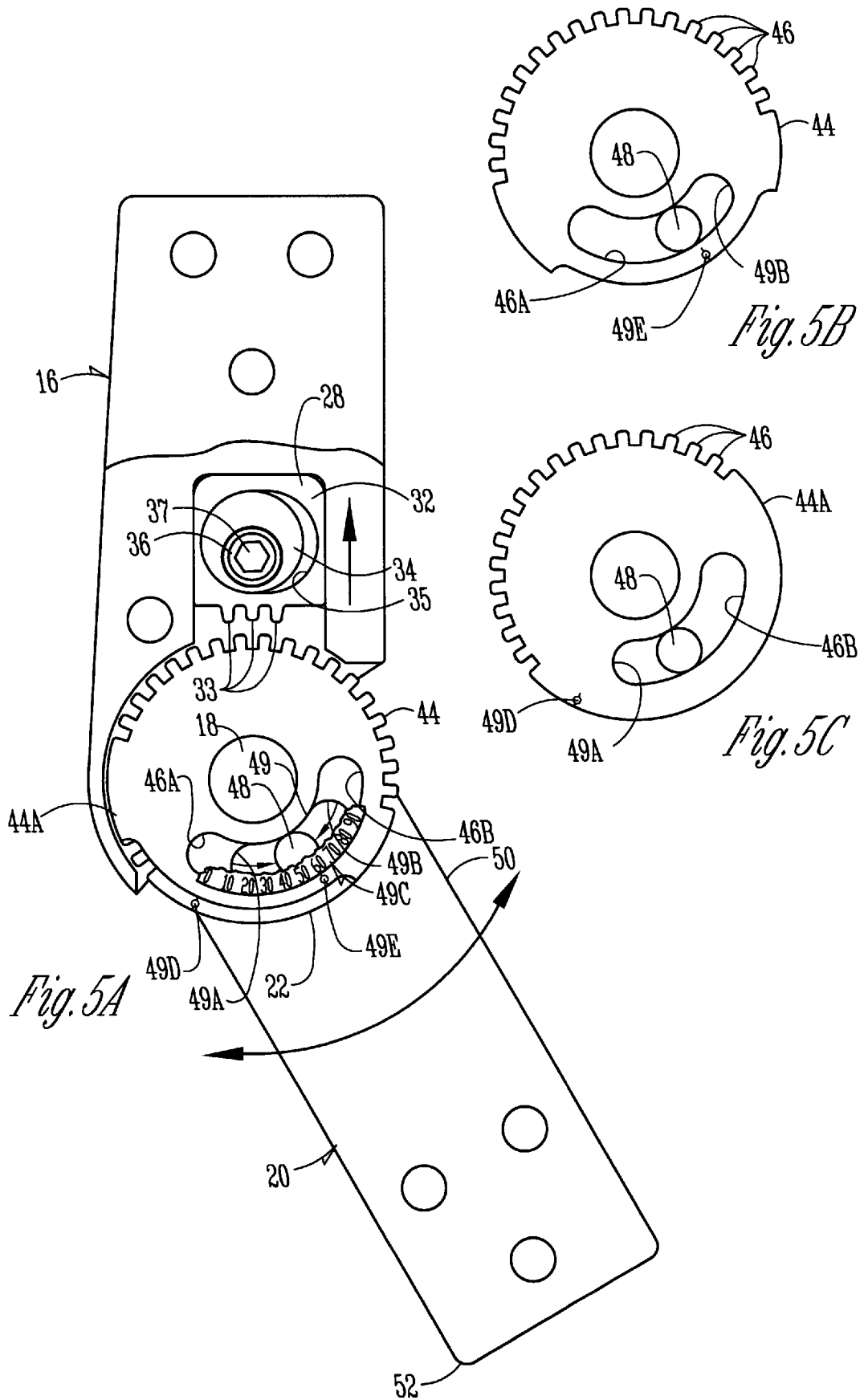

ADJUSTABLE HINGE STRUCTURE

BACKGROUND OF THE INVENTION

Following hip surgery, it is often desirable to be able to move the patient's leg depending from the affected hip to a certain position, and then lock the leg in that position for a predetermined period of time or to limit the leg to a short range of motion for a period of time. Abductor hinges are used to hold the leg in a lateral angular position with respect to the body, and flexion hinges do the same with respect to the forwardly position of the leg.

Existing flexion hinges are often difficult to adjust, particularly by the patient. Also, the hinges are not easily moved only a small increment, and do not easily provide a limited range of motion.

It is therefore a principal object of this invention to provide a flexion hinge that is easily locked and unlocked, and which can be adjusted in fine angular increments to different positions, or a selected range of motion.

This and other objects will be apparent to those skilled in the art.

SUMMARY OF THE INVENTION

A hinge structure has first and second hinge elements having inner and outer ends with the inner ends being pivotally secured together. One of said hinge elements has a series of ratchet teeth associated therewith. The other hinge element has a keeper element slidably mounted thereon to engage, and to be disengaged, with the ratchet teeth to cause the hinge elements to be locked and unlocked, respectively, to each other. A cam element on the hinge structure is operatively connected to the keeper element to slidably move the keeper element into or out of engagement with the ratchet teeth. Separate ratchet rings which have the ratchet teeth have staggered arcuate slots therein, and can be superimposed over each other to provide a generic slot of predetermined length wherein a pin extending therethrough can provide a limited range of motion defined by the length of the generic slot.

BRIEF DESCRIPTION OF THE DRAWINGS

FIG. 5A is a view similar to that of FIG. 4 but shows the hinge in an unlocked condition in a different configuration;

FIG. 5B is a side elevational view of the outer ratchet ring in the position of FIG. 5A; and FIG. 5C is a side elevational view of the inner ratchet ring in the position of FIG. 5A.

DESCRIPTION OF THE PREFERRED EMBODIMENT

Figure 1:
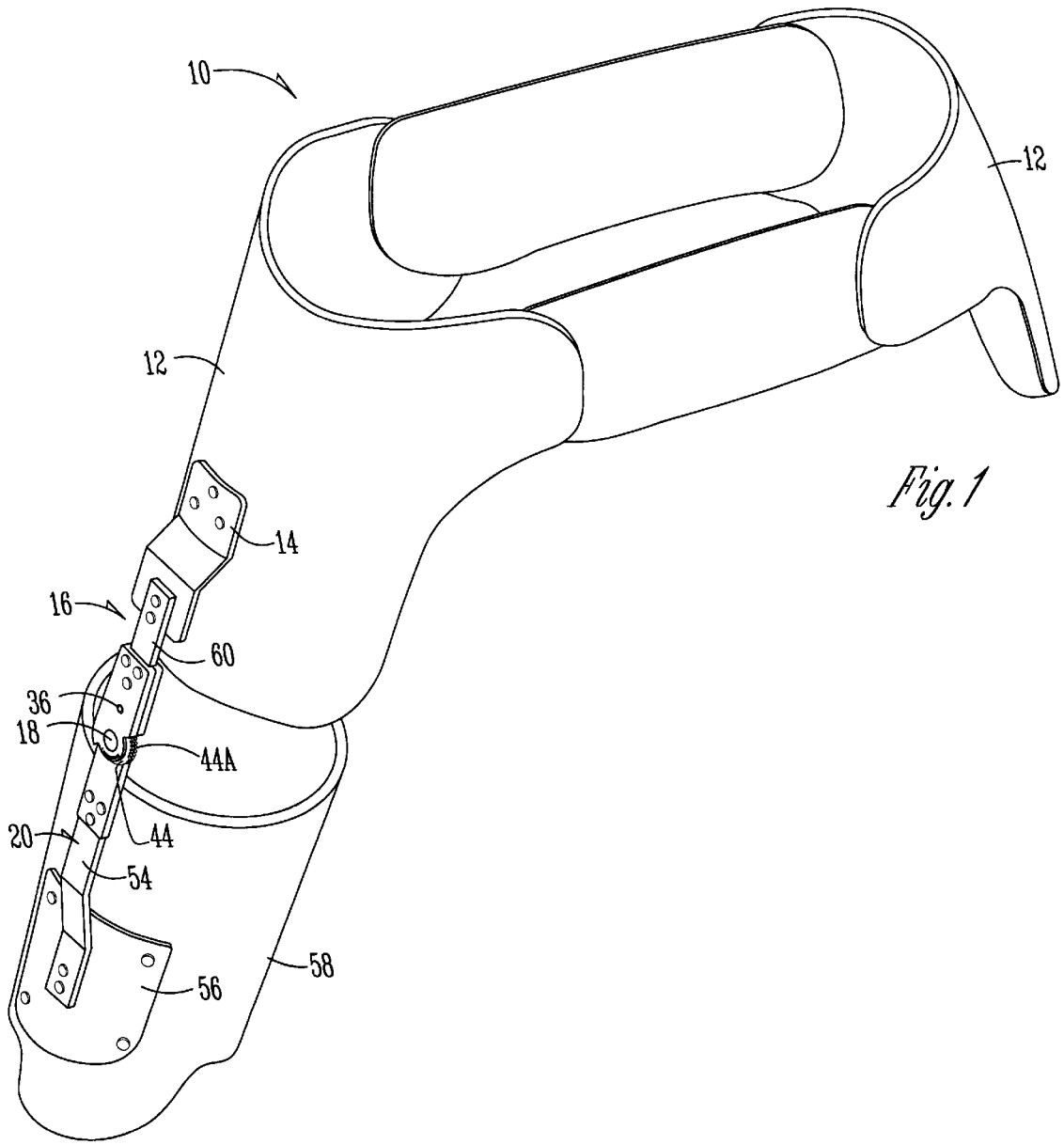
FIG. 1 is a perspective view of a hip stabilizer showing the invention herein.

The conventional hip stabilizer 10 has conventional hip portions 12 secured thereto with the hip stabilizer and hip portions extending around the lower waist of the patient. An upper bracket 14 is riveted or otherwise secured to the hip portion 12 and is rigidly secured by riveting or the like to an upper hinge element 16. A pin 18 extends through the hinge element 16 and a conventional keeper screw 18A is threaded into one end of pin 18 to secure the upper hinge element 16 to the lower hinge element 20.

Figure 2:
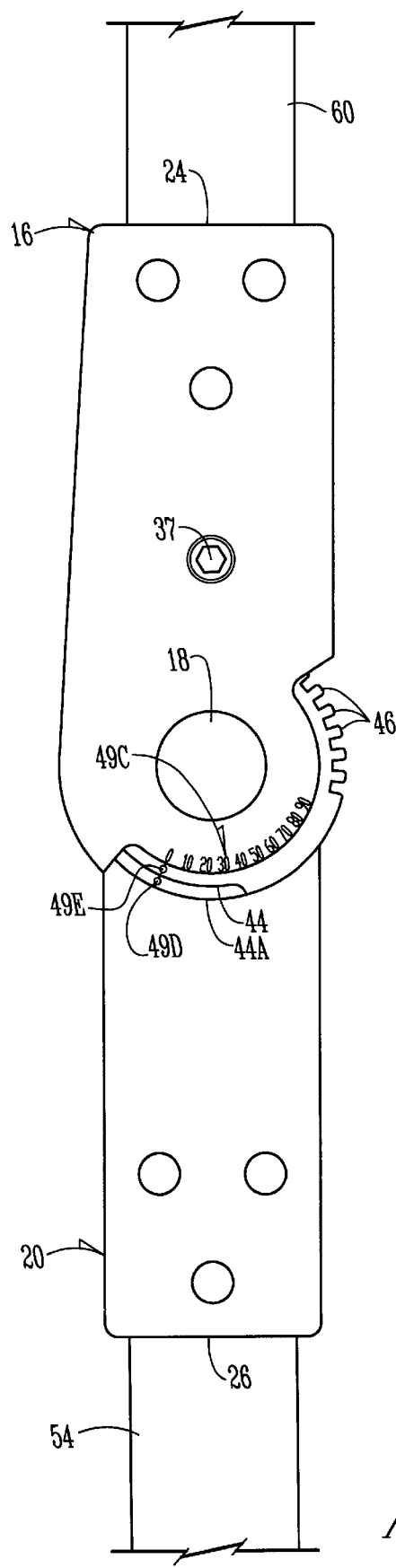
FIG. 2 is an enlarged scale partial side elevational view of the hinge shown in FIG. 1.
Figure 3:
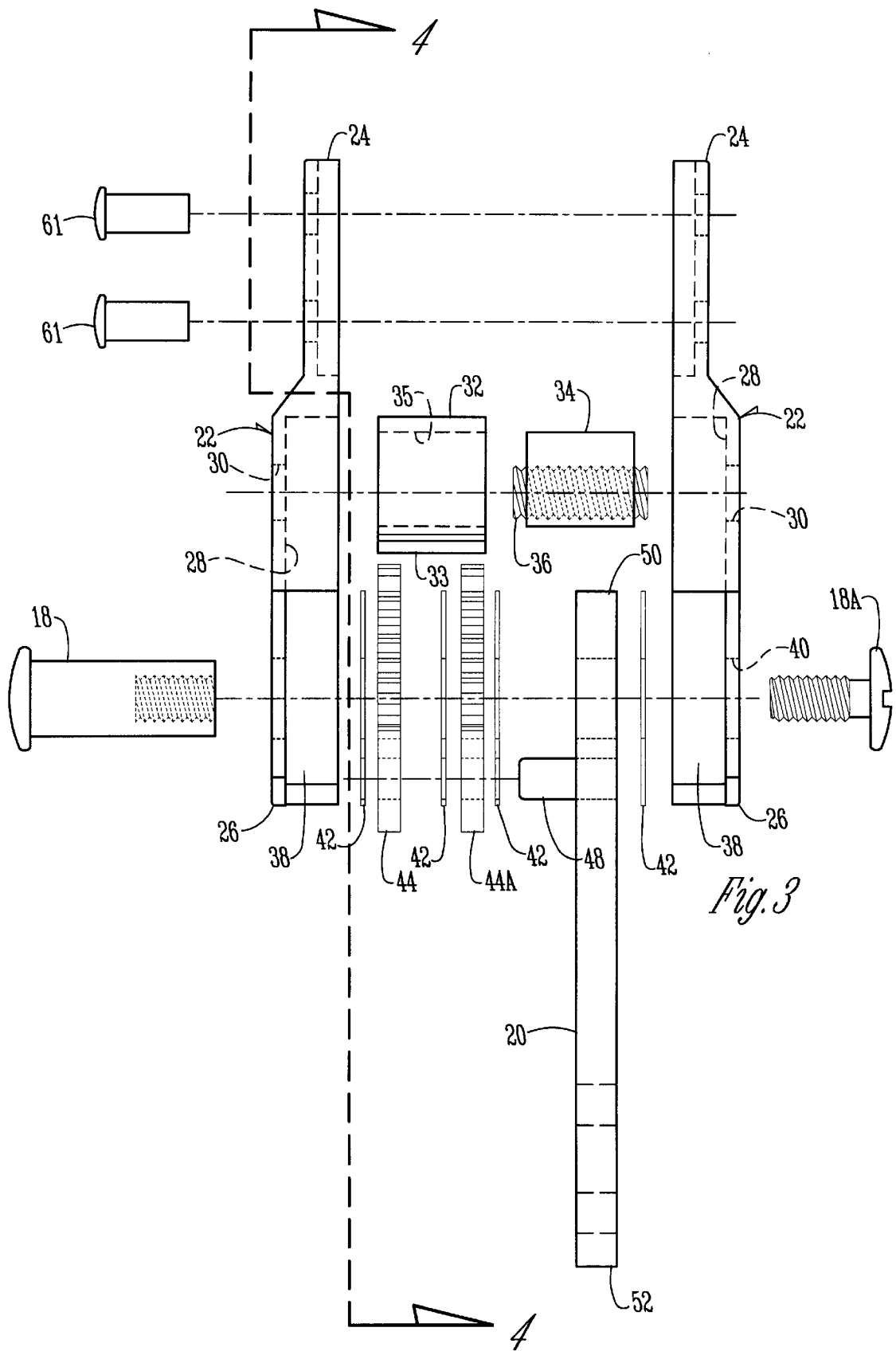
FIG. 3 is an exploded view of the components of the hinge.

The upper hinge element 16 includes upper hinge sections 22 which have upper ends 24 and lower ends 26. Each of the hinge sections 22 have first sockets 28. Each of the first sockets 28 have apertures 30 therein. A keeper block 32 is slidably mounted within the first sockets 28. The keeper block 32 has downwardly extending teeth 33 thereon. A cam cylinder 34 is rotatably mounted within a bore 35 extending laterally through the keeper block 32. An allen screw 36 is rotatably mounted on an offset axis in cam cylinder 34 and has an allen wrench socket 37 in at least one end thereof (FIGS. 2 and 3).

An inner socket 38 is located in each of the hinge sections 22. The inner sockets 38 have centered apertures 40 which are adapted to receive pin 18. Mounted on pin 18 when the aforesaid components are assembled are a plurality of washers 42 and ratchet rings 44 and 44A which have a segment of their periphery formed in the shape of a plurality of ratchet teeth 46.

Arcuate slot 46A appears in the outward ratchet ring 44 (FIG. 5) and arcuate slot 46B appears in inner ring 44A. Both slots scribe an arc of 90°. A pin 48 secured to lower hinge 20 extends through slots 46A and 46B. The rotational position of the rings 44 and 44A can be staggered to create an effective "generic" slot 49 with ends 49A and 49B. End 49A is the lower end of slot 46B (FIG. 5C) and end 49B is the upper end of slot 46A (FIG. 5B).

Figure 4A:
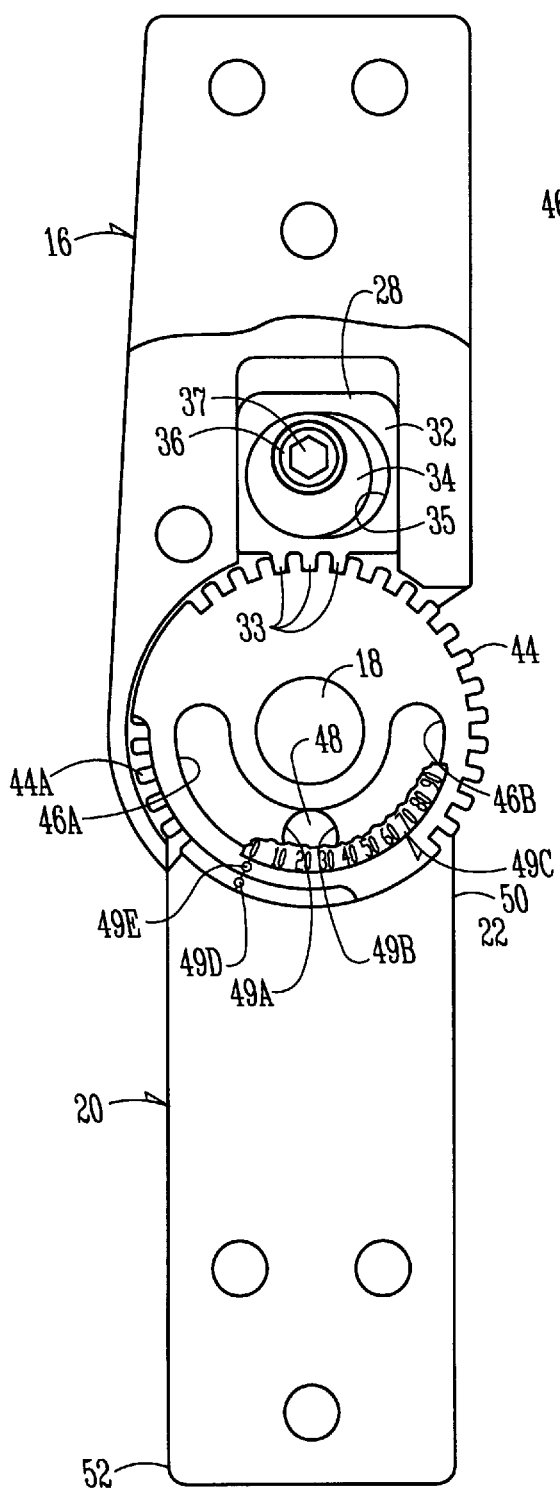
FIG. 4A is a partial sectional view taken on line 4—4 of FIG. 3

A series of indicia marks and numerals 49C extend along a peripheral quadrant of the inner end of one of the hinge sections 22 (FIG. 2) to identify degrees of rotation. An indica mark 49D on inner ring 44A designates a "zero°" position, and an indicia mark 49E on outer ring 44 designates the extent to which the two rings 44 and 44A are offset from each other, whereupon the mark 49E will be adjacent a number on scale 49C which measures the length of generic slot 49. In FIG. 5A, the "length" of slot 49 is approximately 60°. In FIG. 4A, the length of the generic slot 49 is zero, i.e., no slot 49 exists because hinge elements 16 and 20 are in alignment.

The lower hinge element 20 is also mounted on pin 18 and has an inner end 50 and an outer end 52. With reference to FIG. 1, an arm 54 is riveted by its respective ends to the lower hinge 20 and the bracket 56 which is riveted or otherwise secured to the leg portion 58 of the device. An upper arm 60 (FIG. 1) is riveted by its ends to bracket 14 and to the upper portions of upper hinge sections 22. See rivets 61 in FIG. 3.

Figure 4B:
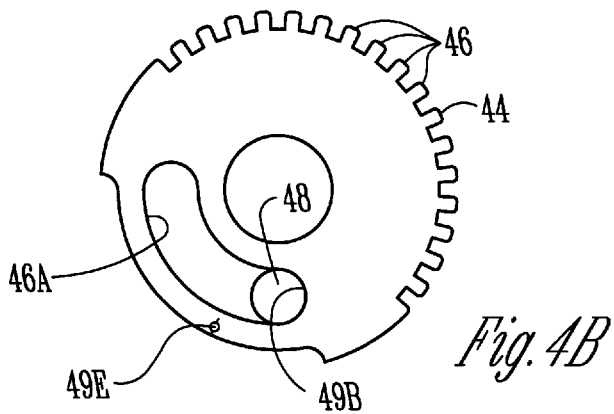
FIG. 4B is a side elevational view of the outer ratchet ring in the position of FIG. 4A.
Figure 4C:
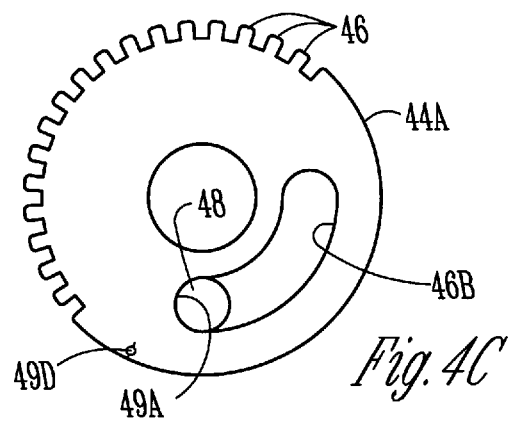
FIG. 4C is a side elevational view of the inner ratchet ring in the position of FIG. 4A.

The components of FIG. 3 are shown in their assembled condition in FIGS. 1, 2, 4 and 5. The upper hinge element 16 can pivot with respect to the lower hinge element 20 about pin 18 when the components are shown in FIG. 4. In this locked condition, an allen wrench is inserted into the allen wrench socket 37 to move the cam member 34 into the position shown in FIG. 4. This lifts the teeth 33 on keeper 32 upwardly out of inner connection with the ratchet teeth 46 on the ratchet rings 44. When it is desired to move the leg portion 58 at an angular position with respect to the hip stabilizer 10, the allen wrench is placed in wrench socket 37 to rotate the cam member 34 from the position shown in FIG. 4 to the position shown in FIG. 5. This disengages the teeth 33 from the keeper block 32 and frees the lower hinge element 20 to be moved about the axis of pin 18. When the member 20 is in its desired angular relationship with respect to the upper hinge element 16, the allen wrench can again be employed, by rotating the bearing member 34 in the opposite direction, to move into an engaging position where the teeth 33 of the keeper block 32 are in locking engagement with the ratchet teeth 36 of the ratchet ring 44. When this is done, the configuration of FIG. 5 will be in its locked position, or locked with a fixed range of motion, as discussed below.

The range of motion of hinge element 20 with respect to hinge element 16 is created when the generic slot 49 is created as previously discussed. When screw 18A is loosened, the rings 44 and 44A can be manually "dialed" to any desired rotational position with a 90° arc to create the generic slot 49 with a desired radial length within a 90° limit.

From the foregoing, it is seen that the hinge of this invention will be effective to be locked to any configuration within a 90° range limited only by the radial length of generic slot 49. The hinge can then be locked or unlocked as further adjustment may be necessary.

It is therefore clear that this invention will achieve at least all of its stated objectives.

What is claimed is:

1. A hinge structure, comprising, a first hinge element having inner and outer ends, a second hinge element having inner and outer ends, the inner ends of said hinge elements being superimposed over each other and pivotally secured to each other, said first hinge element having a plurality of ratchet teeth operatively associated therewith and disposed in an arcuate pattern on its inner end, said second hinge element having a keeper element movably secured on its inner end, and a cam element rotatably mounted on said hinge structure for slidably moving said keeper element into locking engagement with said ratchet teeth to lock said first and second hinge elements together, and to move said keeper element out of engagement with said ratchet teeth to unlock said first and second hinge elements for pivotal movement with respect to each other.

2. The device of claim 1 wherein the range of motion of the first and second hinge elements is limited to 90° or less by a pin secured to one of said hinge elements extending through an arcuate 90° slot on the other of said hinge elements.

3. The device of claim 1 wherein said hinge elements are pivotally secured together by a horizontally disposed first pin, a pair of ratchet rings with ratchet teeth on a portion of their peripheral edges, oppositely located overlapping arcuate slots in said rings, a second pin on said second hinge element and extending through said arcuate slots, said rings being rotatable on said first pin to permit adjustment in the degree to which said arcuate slots overlap to create a generic slot to be formed around said second pin defined by the spaced distance between one end of each of said arcuate slots, and means for locking said rings in position to fix the length of said generic slot.

4. The device of claim 1 wherein an indicia scale is located on one of said hinge elements with a separate indicia mark on each of said rings associated therewith so that the extent of overlap of said arcuate slots can be visually determined.

* * * * *